United States Patent [19]

Chang et al.

[11] Patent Number: 4,952,508
[45] Date of Patent: Aug. 28, 1990

[54] **METHOD AND VECTOR ORGANISM FOR CONTROLLED ACCUMULATION OF CLONED HETEROLOGOUS GENE PRODUCTS IN *BACILLUS SUBTILIS***

[75] Inventors: Shing Chang, Oakland; Hing C. Wong, San Ramon; Vaughan P. Wittman, Napa, all of Calif.

[73] Assignee: Cetus Corporation, Emeryville, Calif.

[21] Appl. No.: 64,841

[22] Filed: Jun. 19, 1987

Related U.S. Application Data

[63] Continuation-in-part of Ser. No. 461,248, Jan. 26, 1983, abandoned, which is a continuation of Ser. No. 221,800, Dec. 31, 1980, abandoned, which is a continuation-in-part of Ser. No. 128,537, Mar. 10, 1980, abandoned.

[51] Int. Cl.$^5$ .................... C12P 21/00; C12N 15/00; C12N 1/20
[52] U.S. Cl. .................... 435/252.3; 435/69.1; 435/71.2; 435/172.3; 435/252.31; 435/252.33; 435/320
[58] Field of Search .............. 435/68, 70, 71, 91, 435/172.1, 172.3, 252.3, 252.31–252.35, 320, 69.1, 71.1, 71.2; 935/40, 43, 72–75

[56] References Cited

U.S. PATENT DOCUMENTS

| | | | |
|---|---|---|---|
| 4,237,224 | 12/1980 | Cohen et al. | 435/68 |
| 4,666,848 | 5/1987 | Gelfand et al. | 435/172.3 |
| 4,792,523 | 12/1988 | Wong et al. | 435/68 |

FOREIGN PATENT DOCUMENTS 2048894 12/1980 United Kingdom ............ 435/172.3

OTHER PUBLICATIONS

Itakura et al.; Science, 198:1056, (1977).
Yansura et al.; Proc. Natl. Acad. Sci., U.S.A., 81:439, (1984).
Yansura et al. in Genetics and Biotechnology of Bacilli, 1984, Ganesan et al. (ed.), Academic Press, Inc., New York, N.Y., pp. 249–263.
Imanaka et al.; J. Bacteriol., 147:776, (1981).
Sherratt et al., Journal of General Microbiology, (1973), 76:217–230.
Taniguchi et al., Proc. Japan Acad., Ser. B, 55:464 (1979).
Gray and Chang, J. Bacteriol., 145:422–428, (1981).
Hori and Osawa, Proc. Natl. Acad. Sci., U.S.A., 76:381–385 (1979).
Keggins et al., Proc. Natl. Sci., U.S.A., 75:1423 (1978).
Erlich, Proc. Natl. Acad. Sci., U.S.A., 74:1680 (1977).
Erlich, Proc. Natl. Acad. Sci., U.S.A., 75:1433 (1978).
Gryczan et al., Proc. Natl. Acad. Sci., U.S.A., 75:1428 (1978).
Duncan et al., Chem. Abstr., 86:185728K (1977).
Kreft et al., Chem. Abstr., 89:103524r (1978).
Rothstein et al., Methods in Enzymology, 68:98 (1979).
Lovett et al., Methods in Enzymology, vol. 69:342 (1979).
Rubin et al., Chem. Abstr., 93:14613p (1980).
Gryczan et al., Molec. Gen. Genet., 177:459 (1980).
Gryczan et al., J. Bacteriol., 141:246 (1980).
Young et al., Genetic Engineering, Chakrabarty (ed.), CRC Press, 1978, pp. 145–157.
Johnson et al., Methods in Enzymol, 65:839–856 (1980).
Kroyer and Chang, Gene, 15:343–347 (1981).
McLaughlin et al., Nucleic Acids Res., 10:3905–3919 (1982).
Wong and Chang, Proc. Natl. Acad. Sci., U.S.A., 83:3233–3237 (1986).
Himeno et al., J. Bacteriol., 168:1128–1132 (1986).

*Primary Examiner*—James Martinell
*Attorney, Agent, or Firm*—Lisabeth F. Murphy; Jane R. McLaughlin; Albert P. Halluin

[57] ABSTRACT

A method and a cloning vector are described for the controlled accumulation of cloned heterologous gene products in *Bacillus subtilis*. The cloning vector is capable of being replicated in *B. subtilis* and includes the heterologous gene located and oriented such as to be under the control of an operator, promoter, and ribosome binding site sequence. The gene codes for a protein which is under the control of a transport mechanism by which the protein is secreted by the *B. subtilis*. The gene product is recovered from the growth medium for the *B. subtilis*. The cloning vector is also capable of similar use in other bacteria such as *E. coli*.

8 Claims, 5 Drawing Sheets

FIG. 2

| AMINO ACID POSITION NO. | 1 | 2 | ...... | 61 | 62 | 63 | .... | 116 | – | 117 | .... | 222 | – | 223 | ... | 265 |
|---|---|---|---|---|---|---|---|---|---|---|---|---|---|---|---|---|
| AMINO ACID SEQUENCE | Lys | -Thr | ...... | Glu | -Asp | -Leu | .... | Gly | - | Pro | ..... | Trp | - | Pro | .... | Lys |
| NUCLEOTIDE SEQUENCE | AA$^A_G$ | -ACN | ..... | GAA | -GAT | -CTN | ... | GGN | - | CCN | ... | TGG | - | CCN | ... | AA$^A_G$ |
| RESTRICTION SITE | | | ................ | Bgl II | | | ......... | Sau 96 I | | | ..... | Hae III | | | ......... | |

Arrows point from GAA-GAT-CTN to Bgl II, GGN-CCN to Sau 96 I, and TGG-CCN to Hae III.

FIG. 3

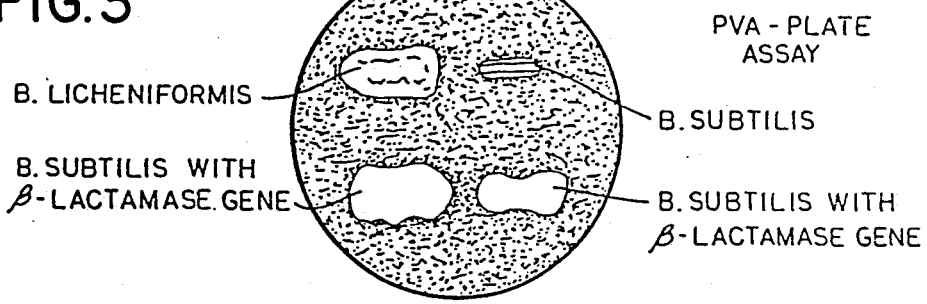

PVA – PLATE ASSAY

B. LICHENIFORMIS
B. SUBTILIS
B. SUBTILIS WITH β-LACTAMASE GENE
B. SUBTILIS WITH β-LACTAMASE GENE

FIG. 5

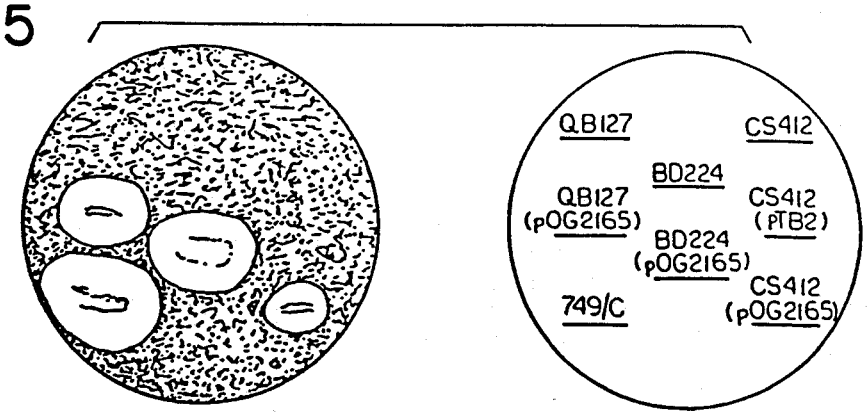

QB127      CS412
QB127 (pOG2165)   BD224   CS412 (pTB2)
         BD224 (pOG2165)
749/C              CS412 (pOG2165)

B. LICHENIFORMIS PEN P GENE

BETA LACTAMASE PROMOTER SEQUENCE:

```
                          -35
GGTCATCATTTCCTTCCGAAAAACGGTTGCATTTAAATCTTACATATGTAATACTTTCA     60
CCAGTAGTAAAGGAAGGCTTTTTGCCAACGTAAATTTAGAATGTATACATTATGAAAGT
    penP                  Hinf            -10  OPERATOR AAGACTACATTTGTAAGATTTGATGTTTGAGTCGGCTGAAAGATCGTACGTACCAATTAT    120
TTCTGATGTAAACATTCTAAACTACGAAACTCAGCCGACTTTCTAGCATGCATGGTTAATA TGTTTCGTGATTGTTCAAGCACTAACAAGTTCGGTGATAGTAGGGATAGTCACGAAGAGTGCTTCATCTGG    180
ACAAAGCACTAACAAGTTCGTGATTGTTCAAGCACTAACACCTTTCTCACGAAGTAGACC TTACGATCAATCAAATATTCAAAGGGAGGACGATTTGATGAAATTATGGTTCAGTA       240
AATGCTAGTTAGTTTATAAGTTTCCCTCCTGCTAAACTACTTTAATACCAAGTCAT
                            222            fMetLysLeuTrpPheSer
                                            |SIGNAL PEPTIDE  5

↓
CTTTAAAAACTGAAAAAGGCTGCAGCAGTGTTGCTTCTCTTGCGTTGGCGCTTGCAGGAT    300
GAAATTTTGACTTTTTCCGACGTCGTCACAACGAAGAGAACGCAGCGCGAACGTCCTA
ThrLeuLysLysAlaAlaAlaValLeuLeuPheSerCysValAlaLeuAlaGly
         10             Pst I         20                25

GCGCTAACAATCAAACGAATGCCTCGCAACCCTGCCGAGAAGAATGAAAAGACGGAGATGA    360
CGCGATTGTTAGTTTGCTTACGGAGCGTTGGACGGCTCTTCTTACTTTTCTGCCTCTACT
AlaAsnAsnGlnThrAsnAla|SerGlnProAlaGluLysAsnGluLysThrGluMet
   30 SIGNAL PEPTIDE   35 MATURE PROTEIN  40                45

AAGATGATTTTGCAAAACGTTGAACTCCTTGTTAAACTAGCTTTGAGCCCTAGAACGTAACC    420
TTCTACTAAAACGTTTTGCAACTTGAGGAACAATTTGATGCAAACGTTTTGATCGAAACGTTGCA
LysAspAspPheAlaLysLeuGluGlnPheAspAlaLysLeuGlyIlePheAlaLeu
            50                  55             60           65

ATACAGGTACAAACCGG.......
TATGTCCATGTTTGGCC.......
AspThrGlyThrAsnArg
     70
AMINO ACIDS
```

FIG. 6

```
                              TGCTGCAGCCTTTTTCAGTTTTAAAGTACTGAACCATAATTTCAT
                              AlaAlaAlaLysLysLeuLysLeuThrSerPheTrpLeuLysMet

CAAAATCGTCTCCCTCCGTTTGAATATTTGATTGATCGTAACCAG

91
ATGAAGCACTCTTTCCACTATCCCTACAGTGTTATGGCTTGAACAATCACGAAACAATAATTGGTACGTACGATC

TTTCAGCCGACTCAAACAT|CAAATCTTACAAATGTAGTCTTTG|AA
                              Operator -10                      -35
211
AGTATTACATATGTAAGATTTAAATG|CAACCGTTTTTTCGGAAGGAAATGATGACCTCGTTTCCACCGGGGACAA
   Operator

ATGAACGGAGGGAAGTGATGGAATTAAAAATGCAGAACTGCATG

331
TTCACTCCAGTTAAATTGACTTCTTAAAATGGCAAACCTATAATGA|GAGTATTACATTTGTAAGTATAGGATG|AT
             \_____/                    \_____/      Operator
              -35                        -10

TAAAATGAAAAAAATACCTCAAATCTCTGATGCGGAATTAGAAGT
   MetLysLysIleProGlnIleSerAspAlaGluLeuGluVal

T
451                                                             ↑
GATGAAAGTCATCTGGAAGCATTCTTCGATCAATACCAATGAGGTAATTAAAGAGTTACCCAAAACCAGTACATGG
  MetLysValIleTrpLysHisSerSerIleAsnThrAsnGluValIleLysGluLeuProLysThrSerThrTrp
                                                                      Ser

AGCCCTAAAACCATCCAAACCATGCTGCTGCGCCTCATTAAAAA
SerProLysThrIleGlnThrMetLeuLeuArgLeuIleLysLys

671
AGGCGCTTTAAACCACCATAAAGAAGGACGGGTTTTCGTTTACACACCAAATATAGACGAAAGTGATTATATAGAG
  GlyAlaLeuAsnHisHisLysGluGlyArgValPheValTyrThrProAsnIleAspGluSerAspTyrIleGlu

GTTAAGAGTCACAGTTTTTTAAACCGGTTTTACAATGGAACTCT
ValLysSerHisSerPheLeuAsnArgPheTyrAsnGlyThrLeu

GG
791     ↑↑
TAATTCGATTCTATTAAACTTTTTGGAGAATGATCAGCTGTCAGGTGAAGAAATTAATGAATTGTATCAAATATTA
 AsnSerIleLeuLeuAsnPheLeuGluAsnAspGlnLeuSerGlyGluGluIleAsnGluLeuTyrGlnIleLeu
      MetVal

GAAGAACATAAGAACAGAAAGAAGGAATGA
GluGluHisLysAsnArgLysLysGlu***
```

FIG. 7

METHOD AND VECTOR ORGANISM FOR CONTROLLED ACCUMULATION OF CLONED HETEROLOGOUS GENE PRODUCTS IN BACILLUS SUBTILIS

This application is a continuation-in-part of application Ser. No. 461,248, filed Jan. 26, 1983, now abandoned, which is a continuation of application Ser. No. 221,800, filed Dec. 31, 1980, now abandoned, which is a continuation-in-part of application Ser. No. 128,537, filed Mar. 10, 1980, now abandoned.

This invention relates to molecular biology and, more particularly, to the so-called art of recombinant DNA. Specifically, the invention relates to a method and a cloning vector for the controlled accumulation of cloned heterologous gene product in *Bacillus subtilis* and other bacteria, thereby facilitating the recovery of the gene product.

The invention discloses three unique genetically engineered plasmids. Organisms containing these plasmids have been deposited with the American Type Culture Collection, Rockville, Md., 20852. They have been assigned ATCC numbers: 31,776–31,778. ATCC number 31,776 has been assigned to plasmid pOG1196; number 31,777 has been assigned to plasmid pOG2165; and number 31,778 has been assigned to plasmid pOG2110. These cultures have been accepted for deposit under the Budapest Treaty and Applicants have directed that the plasmids be available without restriction to the general public upon the issuance of a United States patent.

As is well known, the particular sequence of amino acids in a given protein is determined in accordance with the code carried in the gene for that protein. In the process of translation by which proteins are formed from DNA, via messenger RNA, groups of three nucleotides in the DNA, called codons, each place one of twenty possible amino acids at a corresponding position in the protein chain.

With the advent of recombinant DNA techniques, genetic changes may be made deliberately by the introduction of a predetermined nucleotide sequence, either synthesized or isolated from one strain or species, into the genetic makeup of another strain or species. The known nucleotide sequence may be selected to cause the strain or species into which it is introduced to produce, as part of the translation process, the protein encoded by the known nucleotide sequence. When the modified strain or species proceeds with the normal replication process, it also then duplicates the inserted sequence.

Recombinant DNA techniques involve isolating a suitable piece of a DNA chain (a cloning vector) and breaking or severing the two strands of DNA of the cloning vector at the desired location where the foreign DNA is to be inserted. To do this, particular types of proteins, called restriction enzymes, are typically used. Restriction enzymes will break the DNA at particular nucleotide sequences, although with some restriction enzymes the break may not necessarily occur at the same point on the two intertwined DNA strands. In such a case, if two different types of DNA are severed in a similar manner, the open ends will be complementary and will, under suitable conditions, stick together with the complementary ends lying side by side. They may then be linked together enzymatically (with ligase). This makes it possible to recombine two DNA segments from any source into a single DNA molecule.

Once the DNA vector has been isolated and the foreign piece inserted therein, the recombinant DNA is then placed into a suitable host organism. In order for the host organism to replicate the inserted DNA, it is necessary that the recombinant DNA be inserted into the host in such a way as to become part of its genetic system.

For example, in the bacterium *Escherichia coli*, two convenient types of cloning vectors have been utilized. *E. coli* bacteria, in addition to the main DNA chain or chromosome, frequently have one or more independently replicating circular loops of DNA known as plasmids. Also, a certain type of virus known as a lambda bacteriophage (phage) is also capable of infecting *E. coli* and becoming part of its genetic system. Recombinant DNA techniques have included the use of a variety of plasmids or phages as cloning vectors. This involves the isolation of plasmids or phages from the bacteria, the breaking open of the isolated DNA by restriction enzymes, the insertion of a foreign or heterologous piece of DNA into the plasmid or phage, the restoration of the circular form of the plasmid or the phage structure, and the return of the plasmid or phage to the *E. coli* cell. Once in the host, the heterologous DNA is not only replicated from generation to generation, but also will produce the protein for which it codes if the proper reading frame and promoters exist.

Once heterologous DNA has been successfully recombined into a host microorganism, and the microorganism has produced the cloned gene product, the desired product must be recovered. To do this it has, up to the present invention, been necessary to destroy the cells producing the desired product in order to harvest the product itself. Also, because cells naturally contain a great many different proteins, the isolation process for the desired product may be difficult or complex. Finally, the desired product may be detrimental to the host cell, particularly if it is produced at a high level. In some cases, this may result in the cells activating a defensive mechanism to degrade the desired product.

Most recombinant DNA work to date has been carried out with *E. coli*. *E. coli* is a member of the Gram-negative class of bacteria which contain two layers of membranes enclosing a periplasmic space. Many of the products produced in *E. coli* are secreted into this periplasmic space, if secreted at all. Few products are secreted outside the living cells into the growth media.

On the other hand, *Bacillus subtilis* is a member of the Gram positive class of bacteria which contain only a single layer of bacterial membrane. Thus *B. subtilis* can produce large amounts of protein which are secreted directly into the growth media. Although the general approach to gene cloning in *E. coli* is applicable to *B. subtilis*, attempts to produce a useful product of heterologous gene cloned into *B. subtilis* and secreted into the growth media have thus far been unsuccessful. B. subtilis is somewhat preferable to *E. coli* because of a greater efficiency for plasmid mediated transformation and because it is non-pathogenic.

It is an object of the present invention to provide an improved method for producing heterologous protein by microorganisms.

Another object of the invention is to provide a method for regulating production of a predetermined protein through expression by *B. subtilis*, such protein being non-indigenous to *B. subtilis*.

A further object of the invention is to provide a method for producing protein by *B. subtilis* wherein the protein is non-indigenous to the host species and is secreted into the growth media.

Another object of the invention is to provide a method for producing protein by *E. coli* wherein protein is non-indigenous to the host species and is secreted into the periplasmic space.

A further object of the invention is to provide a plasmid for producing a predetermined protein through expression by *B. subtilis* or *E. coli*, such protein being non-indigenous to *B. subtilis*.

Other objects of the invention will become apparent to those skilled in the art from the following description, taken in connection with the accompanying drawings wherein:

BRIEF DESCRIPTION OF THE DRAWINGS

FIG. 2 is a schematic drawing indicating correspondence between a number of the nucleotide sequences in the fragment of FIG. 1 and protein sequence present in the protein for which the fragment codes, and also indicating the corresponding restriction enzyme recognition sites;

FIG. 3 is a drawing indicating the typical appearance of plates upon which *Bacillus subtilis* strains harboring the recombinant plasmids are grown, as the plates appear after PVA assay for beta-lactamase activity;

FIG. 5 is a drawing indicating the typical appearance of plates upon which various bacterial strains harboring the recombinant plasmids are grown, as the plates appear after PVA assay for beta-lactamase activity;

FIG. 6 is a diagram of the nucleotides comprising a portion of the *B. licheniformis* penP gene, and the operator region, promoter ($-35$ and $-10$ regions), and ribosome binding sequence (including the ShineDalgarno and transcription initiation start codon) of the penP gene; and FIG. 7 is an illustration of the complete nucleotide sequence of penI and a partial nucleotide sequence for penP. Nucleotide sequence, amino acid sequence, ribosome binding site sequence, and the promoter ($-35$ and $-10$ regions) for penP as well as the nucleotide and amino acid sequences, ribosome binding site sequence and putative promoter for penI are indicated.

DETAILED DESCRIPTION OF THE INVENTION

Figure 1:
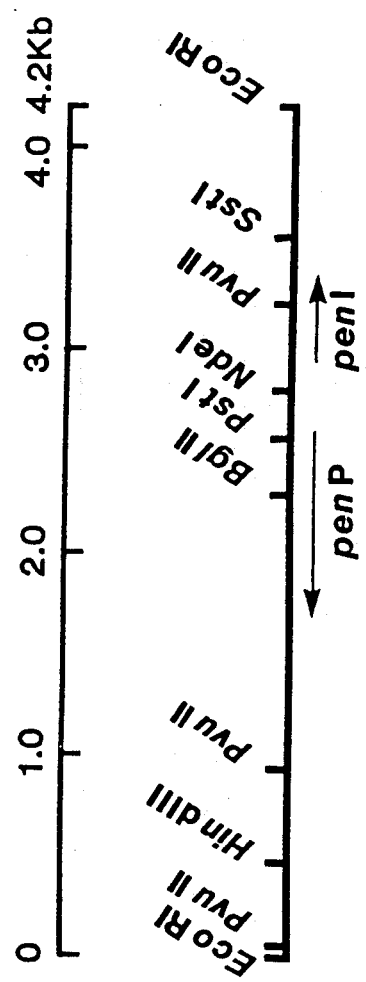
FIG. 1 is a schematic drawing providing a partial structural map of a DNA fragment which contains the genes for beta-lactamase (penP), also referred to herein as penicillinase, and the penicillinase repressor (penI) obtained from *Bacillus licheniformis*. The arrows indicate direction of transcription and location of the penP and penI genes.

Very generally, and in accordance with one form of the invention, a predetermined protein which is non-indigenous to *B. subtilis* is produced through expression by *B. subtilis*. Growth media and conditions are provided for growing a strain of *B. subtilis* in which a plasmid has been introduced. The plasmid is capable of being replicated in the strain and has a gene therein for the predetermined protein. The gene is located and oriented in the plasmid such as to be under the control of an operator, promoter, and ribosome binding site sequence. The protein is also under the control of a transport mechanism by which the protein is secreted by the host strain. Upon secretion, the protein is recovered from the growth media.

When, according to the invention, the predetermined protein is expressed in a Gram-negative bacteria, such as *E. coli*, the protein is again transported across the bacterial membrane by the signal peptide. However, here the protein is "secreted" into the periplasmic space instead of the growth media since the Gram-negative bacterium has an outer membrane in addition to its normal cytoplasmic membrane. The predetermined protein can be recovered from the periplasmic space.

The method of the invention necessitates the use of a cloning vector containing a sequence of nucleotides capable of initiating the transcription and translation process. These nucleotides, which provide an operator, promoter, and ribosome binding site sequence, may be naturally present in the vector, may be inserted therein as a separate segment of DNA using recombinant DNA techniques, or may be part of the heterologous DNA containing the gene of interest. The heterologous DNA, which will contain at least the structural gene for a desired protein product, is placed in the cloning vector so as to be transcribed and translated under control of the operator, promoter, and ribosome binding site sequence. For correct translation of the inserted heterologous DNA, the nucleotides in the inserted DNA must be in the correct reading frame. In addition, it may be desirable or even necessary that the cloning vector include a sufficient number of nucleotides indigenous to the host cell to ensure read-through translation from the operator, promoter, and ribosome binding site sequence into and through the inserted heterologous DNA in the correct reading frame.

In accordance with the invention, the cloning vector utilized includes a sequence of nucleotides which comprise codons for a functional transport signal peptide sequence. Signal peptide sequences are typically short leader sequences of amino acids on newly made secretory proteins. Although the mechanism by which the transport signal peptide sequence operates is not entirely understood, it is believed that the transport protein is excreted by the cell and directs that protein appended to it from the cytoplasm as the protein is made. Once the transport function has been performed by the transport signal peptide sequence, the transport sequence may be removed by natural processes.

In accordance with the invention, the heterologous DNA can be inserted into the cloning vector at a location which allows the protein for which it encodes to be transported in accordance with the transport signal peptide sequence coded by the signal codons. Thus, the cloned gene product can be conveniently transported to a desired destination from which the gene product may be harvested. This has several advantages. Because the destination is outside the cell, the host cells need not be destroyed to harvest the gene products, thus allowing for the continuous or uninterrupted production of the gene product. Also, since cells contain a great many proteins, the ability to export the cloned gene product makes the isolation and purification of the product a much simpler task. Finally, since cloned gene products, especially if produced at a high level, may be detrimental to the host cells, the ability to harvest the cloned gene products from outside of the cell membranes often means that the products will not harm the cells, nor will the cells possibly produce a defensive enzyme which will degrade the gene product.

The precise location at which the heterologous DNA must be inserted in the cloning vector will, of course, depend upon how the transport signal peptide sequence functions. In some cases, the transport signal peptide sequence will immediately precede the heterologous DNA, either as part of the gene itself or having already been present in the plasmid. The signal sequence itself can constitute the necessary sequence of nucleotides to provide for readthrough translation of the heterologous DNA. On the other hand, there may be some cases in which the transport signal peptide sequence must be located elsewhere than immediately preceding the heterologous DNA. In such cases, it may be necessary to produce the desired peptide sequence with some additional amino-acids at the beginning (coded by the extraneous codons) in order to provide the necessary readthrough functions.

The beta-lactamase regulon defines DNA sequences encoding an operator region that is recognized by a functional penI repressor. There are three such operator regions illustrated in FIG. 7. Each of these three regions is composed of two nearly identical, inverted repeat sequences. For purposes of the present invention, an operator is composed of a pair of inverted repeat sequences such that a functional repressor can recognize and bind this nucleotide region. This regulon can be isolated from the 4.2 kb EcoRI restriction fragment of plasmid pTB2 and converted to an active form as described herein, or alternatively, the regulon can be prepared chemically using conventional chemical synthesis techniques using the information provided by the nucleotide sequence illustrated in FIG. 6. This sequence is available for insertion into any expression vector for the production of a heterologous protein. The vector may contain a replicon functional in a single host, for example, the pBR322 replicon for use in Gram-negative hosts such as *E. coli*, or the vector may be bifunctional containing the *E. coli* replicon as well as a replicon functional in Gram-positive hosts such as species of *Bacillus* and *Streptomyces*.

The expression of the heterologous gene can also be controlled at the molecular level using the penI repressor to inhibit transcription of the gene. The penI repressor is also present on the 4.2 kb EcoRI fragment of plasmid pTB2, although in an inactive form, and the nucleotide coding sequence, as well as its operator, promoter, and ribosome binding sequence are illustrated in FIG. 7. The penI repressor is available for use on a HindIII-BamHI cassette fragment as described in Example 7, and can be subcloned into an appropriately digested vector and used to transform a host which carries the penP operator which is operably linked to a promoter and to the heterologous gene sequence to be expressed. It is intended that the repressor gene can either replicate independently on a vector or can integrate into the host's chromosome.

The following examples illustrate other specific instances in which the invention may be employed, but are not intended to limit the scope of the invention:

EXAMPLE 1

Figure 4:
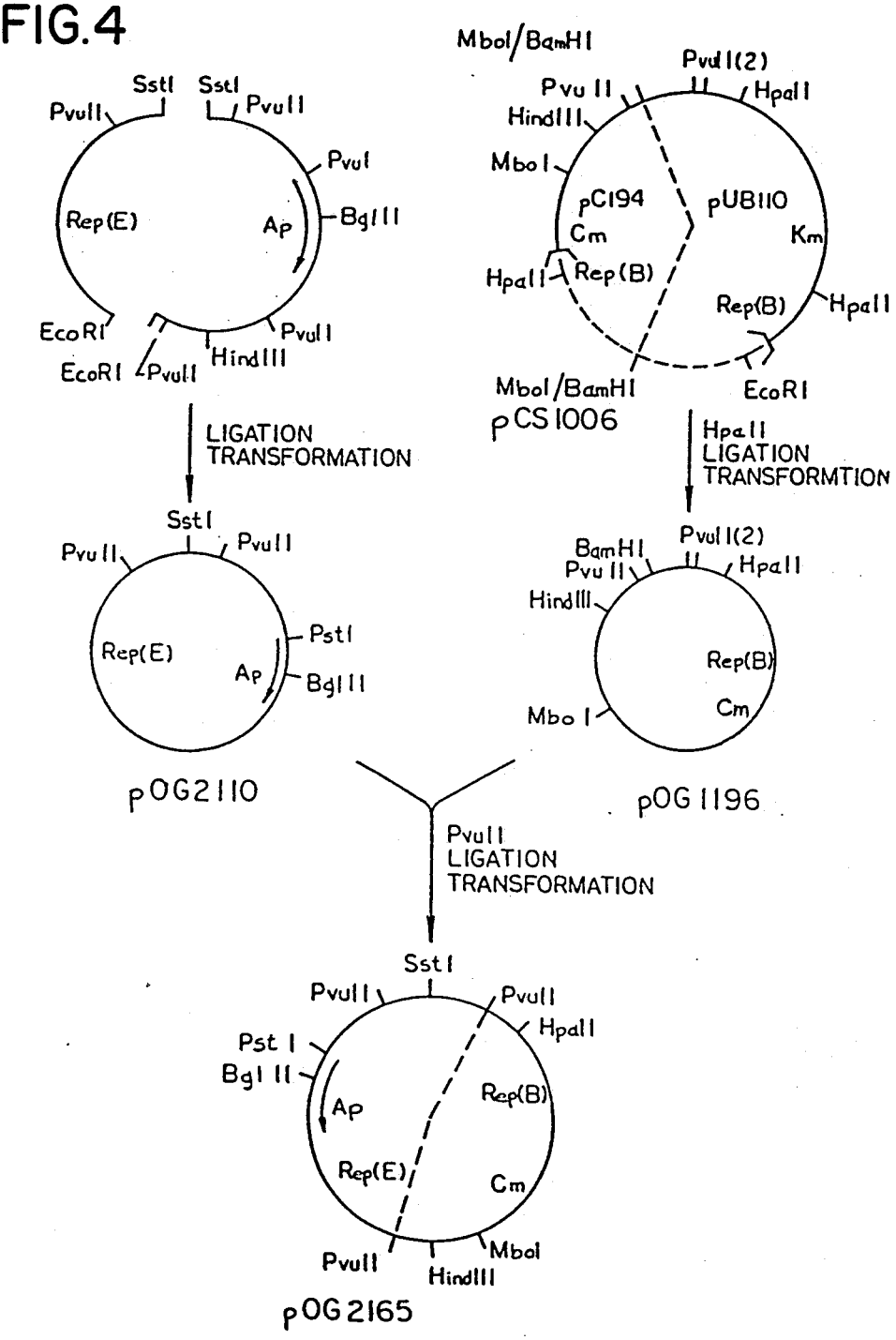
FIG. 4 is a schematic illustration of the construction of *E. coli* plasmid pOG2110, *B. subtilis* plasmid pOG1196, and the bifunctional plasmid pOG2165.

In order to provide a plasmid for producing a predetermined protein non-indigenous to a host organism, a plasmid vector containing the *B. licheniformis* beta-lactamase gene was made and then replicated in both *B. subtilis* and *E. coli*. The plasmid was constructed by purifying a 3.5 kb (kilobase) EcoRI-SstI fragment containing the beta-lactamase gene and then ligating it with a 2.1 kb EcoRI-SstI fragment containing the replication function of the *E. coli* plasmid pOP1Δ6 (described by Gelfand, et al., *Proc. Nat. Acad. Sci. USA* (1978) 75, 5869–5873). Following transformation into competent *E. coli* CS412 cells (an $r_k m_k$ Pro$^-$ derivative of C600) and a growth period adequate for expression (90 minutes), Ap-resistant transformants were obtained. Plasmids from three clones were prepared; one designated as pOG2110 was further characterized. FIG. 4 details the location of the expected and observed restriction sites in pOG2110.

To allow for replication of pOG2110 in *B. subtilis*, a bifunctional replicon was constructed using pOG2110 and the *B. subtilis* plasmid pOG1196. The construction of pOG1196 is summarized in FIG. 4.

Initially a chimeric plasmid (pCS832) containing the entire sequences of plasmids pC194 (Cm®) and pUB110 (Km®) made by ligating the two MboI fragments of pC194 with the BamHI digested pUB110. The resulting plasmid carried both the Cm gene from pC194 and the Km (Nm) gene from pUB110. It has a size of 7.5 kb. A spontaneous deletion mutant (plasmid pCS1006) was obtained form one of the sub-clones. It had lost the HpaII site originated in pC194 and known to be located in the pC194 replication region (Chang and Cohen, *Molec. Gen. Genet.* (1979) 168, 111–115). It still retained the replication function of pUB110 and the two resistance markers. By recircularizing the largest HpaII fragment (3.6 kb) of pCS1006, plasmid pOG1196 was obtained. This plasmid confers only Cm-resistance and possesses the replication function derived from plasmid pUB110. The map of pOG1196 is shown in FIG. 4.

*E. coli* plasmid pOG2110 and *B. subtilis* plasmid pOG1196 contained two and three PvuII sites respectively. Equal amounts of PvuII-digested pOG2110 and pOG1196 plasmid DNA were ligated and used to transform *E. coli* strain CS412. Cm-resistant clones were selected; all were also Ap-resistant. The composite plasmid pOG2165 isolated from one of the Cm-resistant Ap-resistant transformants was studied further. A map of this 7.5 kb plasmid is shown in FIG. 4. Plasmid pOG2165 replicates in both *E. coli* and *B. subtilis* and confers upon either host both Cm-and Ap-resistance.

*B. subtilis* and *E. coli* cells harboring plasmid pOG2165 are resistant to ampicillin as a result of the production of the *B. licheniformis* beta-lactamase enzyme. This can be demonstrated by means of the PVA plate assay developed by Sherratt and Collins (*J. Gen. Microbiol.* (1973) 76:217–230) The positive results obtained from such an assay are illustrated in FIG. 5.

When pOG2165 is propagated in *B. subtilis* BD224, both the membrane-bound and the secreted form of the heterologous beta-lactamase are synthesized. The amount produced by this strain is variable and depends upon the growth conditions used. pOG2165 can also be propagated in *B. subtilis* strain QB127 (Kunst et al., *Bio. Chemie.* (1974) 56 1481-1490) QB127 is a bacterial strain with the sacU$^h$ mutation which causes overproduction of several exoenzymes such as levan-sucrase, alpha-amylase and extracellular proteases. Levels of beta-lactamase detected in cultures of QB127 (pOG2165) are similar to those levels detected in BD224 (pOG2165) cultures under the same conditions.

The bifunctional plasmid pOG2165 itself possesses unique sites for restriction enzymes SstI, HindIII, PstI and BglII. Insertion of DNA into the BglII and the PstI sites leads to inactivation of the *B. licheniformis* beta-lactamase gene and provides an easily recognizable phenotype for identifying clones carrying inserts When the exact reading frame of the DNA sequence to be inserted is known, it is possible to create a fused protein containing the leader sequence and the first 71 amino acid residues of the beta-lactamase exoenzyme by cloning into the BglII site. Fused protein made in this way is secreted by the *Bacillus* cells due to the presence of the leader sequence at the amino terminus. These features make pOG2165 a useful vector for the cloning and efficient expression of heterologous genes, and the subsequent secretion of the gene product in *B. subtilis* and *E. coli*.

On the other hand, when the exact reading frame of the DNA sequence to be inserted is known, and insertion is made at the PstI site, a fused protein is made which will accumulate in the host organism. Since the PstI recognition site is located in the initial portion of the nucleotide sequence coding for the signal peptide, only a portion of this sequence is transcribed before the heterologous gene sequence is encountered. Even though the fused protein is expressed, this portion of the signal peptide is insufficient to confer the normal signal peptide's secretion function. As a result, products of genes inserted at the PstI site accumulate in the host organism.

A portion of the nucleotide sequence comprising the *B. licheniformis* penP gene is diagrammed in FIG. 6. The beta-lactamase promoter region ($-35$ and $-10$ regions) is located between nucleotides 1 and 222; more precisely located between nucleotides 1 and 63, numbered according to FIG. 6, wherein the first nucleotide of the penP coding region is defined as 222. The operator region contains two operators, each operator consisting of two units. This region is bounded by nucleotides 36–82 and is characterized by having twofold symmetric regions within each operator unit. The ribosome binding site sequence is bounded by nucleotides 205–212. The nucleotides which code for the amino acids comprising the signal peptide begin with nucleotide 222 and end with nucleotide 323. As a result, the signal peptide is composed of thirty-four amino acids. The PstI recognition site is located between nucleotide positions 259 and 264, or at amino acids thirteen through fifteen on the signal peptide chain. Insertion of a sequence encoding a heterologous protein at this PstI site results in a fused protein which will be expressed but not transported across the bacterial membrane. Successful secretion requires fusion with either the total signal peptide, or fusion with at least the first twenty-six amino acid residues in the signal peptide chain.

EXAMPLE 2

*B. licheniformis* produces a large amount of beta-lactamase in the secreted form (exoenzyme). The secretion of this protein is believed to be the result of the interaction between the bacterial membrane and the signal peptide sequence which facilitates the transport of the protein across the single bacterial membrane barrier. The beta-lactamase gene was cloned and inserted into plasmids which were capable of being replicated in *B. subtilis*. The plasmids were then transformed into the *B. subtilis* hosts resulting in the secretion of beta-lactamase. This constitutes the first expression of a heterologous gene in *B. subtilis* and the transport of the gene products into the culture or growth media from the *B. subtilis* cells.

To clone the beta-lactamase gene from the *B. licheniformis* strain, total chromosomal DNA from *B. licheniformis* strain 749/C was isolated and digested with EcoRI restriction endonuclease. Chromosomal DNA isolated from *B. licheniformis* 749/C was prepared according to Marmur (*J. Molec. Biol.* (1961) 3:208–18). *E. coli* plasmid pSC101 is isolated from cells using the cleared lysate procedure of Kupersztoch and Helinski (*Biochem. Biophys. Res. Commun.* (1973) 54: 1451–59). Three μg of chromosomal DNA and 2 μg of pSC101 DNA were digested with endonuclease EcoRI and ligated with T4 DNA ligase as described (Hershfield, et al. *Proc. Natl. Acad. Sci.*, USA (1974) 71:3455–59), and transformed into competent cells of *E. coli* strain CS412 (an $r_k m_k Pro^-$ derivative of C600) using the protocol of Cohen, et al. (*Proc. Natl. Acad. Sci., USA* (1972) 69:2110–14).

Transformants resistant to ampicillin a 10 μg/ml were selected and one of the transformants carrying recombinant plasmid designated pTB2 was characterized further. Plasmid pTB2 caries a 4.2 kb EcoRI fragment on the pSC101 vector. This plasmid confers to the host tetracycline (the marker on pSC101) and ampicillin resistances, indicating that the beta-lactamase gene product is made as a functional enzyme which degrades ampicillin in the media.

The beta-lactamase gene including the operator, promoter, and ribosome binding site sequence is located on the 4.2 kb pair EcoRI fragment mentioned above. Subsequent analysis of this fragment using various restriction enzymes and gene cloning permits deduction of the structure of the gene for this enzyme as partially mapped and shown in FIG. 1. The primary sequence of the beta-lactamase from *B. licheniformis* strain 749/C has been previously determined (P. J. Meadway, Ph.D., Thesis, University of Edinburgh, 1969). From the known amino acid sequence, the Gly-Pro (position 116-117) sequence corresponds to the nucleotide sequence GGN-CCN, which in turn is the recognition sequence for endonuclease Sau96I (GGNCC). Similarly, the Trp-Pro (position 222-223) sequence is coded by nucleotide codons TGG-CCN, within which the center tetranucleotide sequence GGCC is recognized and cleaved by endonuclease HaeIII (see Roberts, in *DNA Insertion Elements, Plasmids, and Episomes*, 1977, ed. Bukhari, Shapiro, Adhya, Cold Spring Harbor Lab., p. 757).

The 4.2 kb cloned fragment was analyzed by a number of endonucleases, as listed in FIG. 2, using the conditions specified by the supplier (New England Biolabs, Inc., Beverly, MA 01915, 1978 catalog) The digested DNA was analyzed on agarose gels as described by Sharp, et al. (*Biochemistry* (1973) 12:3055–63), and on acrylamide gels (Maxam and Gilbert, *Proc. Natl. Acad. Sci., USA* (1973) 73:3942–46) The mapping data is summarized in FIG. 2. The Sau96I site and the HaeIII site were located in the 2.3 kb PvuII fragment which contains the complete betalactamase gene sequence. These two sites are separated by 320 nucleotides which is consistent with the protein sequence data (106 amino acids apart)

Plasmid pTB2 carries both the penicillinase gene (penP) and the penicillinase repressor gene (penI) of *B. licheniformis*. Since the penI gene of pTB2 was cloned from *B. licheniformis* strain 749/C, a constitutive strain, it is likely that this allele encoded an inactive repressor (penI$^c$). The nucleotide sequence of the penI allele on pTB2 was determined and found to differ from the wildtype repressor (penI+) sequence (Himeno et al., *J. Bacteriol.* (1986) 168:1128-32) by three nucleotides. Site-directed mutagenesis was used to change the penI$^c$ allele back to the wild-type sequence, as well as to introduce flanking 5' HindIII and a 3' BamHI restriction sites. The wild-type repressor gene was expressed in *E. coli* using a lambda $P_L$ expression vector (pAW740). The purified penI+ protein was shown to bind specifically to the operator sequences preceding the penP gene and the operator preceding the penI gene and was therefore useful to define the operator regions of two beta-lactamase genes. The operator sequences for the penP and penI genes were further defined to the nucleotide level; the nucleotide sequences encoding penI and penP (partial sequence) are presented in FIG. 7.

After identification of the nucleotide sequence which contains the beta-lactamase gene, the gene was cloned into *B. subtilis* using various Bacillus plasmids and using a hybrid *B. subtilis-E. coli* plasmid. Plasmids included pUB110 and pC221 derived plasmids. The *B. subtilis* strains harboring the recombinant plasmids were resistant to ampicillin as well as gave a positive betalactamase reaction on PVA plates (see FIG. 3). Furthermore, beta-lactamase activity was detected in cultures after bacterial cells were removed. This activity clearly indicates the successful expression of the heterologous gene in *B. subtilis*, as well as the transport of the protein through the bacterial membrane into the culture or growth media.

The EcoRI fragment containing the beta-lactamase gene was cloned onto *B. subtilis* plasmid vectors pUB110 (Grycyar and Dubnau, *Proc. Natl. Acad. Sci., USA* (1978) 75:1428-32), and pC221 (Erlich, *Proc. Natl. Acad. Sci., USA* (1977) 74:1680-82) at the respective EcoRI sites using the procedure described above in connection with *E. coli*. Similarly, the 2.3 kb PvuII fragment containing the betalactamase gene has also been cloned onto pUB110 at the PvuII site and the TaqI site.

Ligated DNA preparations were used to transform *B. subtilis* strain BD224 (recE4, trpC2, thr5) by the method of Chang and Cohen (*Molec. Gen. Genet.* (1979) 168:111-15). Transformants resistant to ampicillin on regeneration plates were selected and tested. The production of beta-lactamase is detected by two methods; one is a sensitive plate assay developed by Sherratt and Collins, supra, the other is the iodometric assay described by Ross and O'Callaghan (*Meth. in Enzymology* (1975) 43:69) *B. subtilis* clones resistant to ampicillin gave positive results for both tests. In addition, beta-lactamase activity was also detected in the culture after the cells were removed, indicating that the beta-lactamase is not only made, but also exported in *B. subtilis*.

The cloning of heterologous genes into *B. subtilis* and the functional expression of these genes as intracellular proteins have been shown previously by Keggins et al., *Proc. Natl. Acad. Sci., USA* (1978) 75:1432-27. In this study, however, the cloned genes are genes coding for enzymes which are normally present intracellularly in wild-type *B. subtilis*. The successful expression of genes which are non-indigenous to *B. subtilis*, and the successful secretion of the products of these genes was not demonstrated.

The work on the beta-lactamase gene presented in this Example is the first demonstration that a new function, namely, beta-lactamase production, can be introduced into *B. subtilis* using gene cloning techniques. In addition, this Example constitutes the first demonstration that a foreign gene product can be made to pass through the *B. subtilis* membrane barrier and be secreted as an exo-protein. The beta-lactomase, which is a commercially useful product, is produced by a strain which does not otherwise produce this enzyme.

EXAMPLE 3

The *B. licheniformis* beta-lactamase gene described in Example 2 was also inserted into plasmids capable of being replicated in *E. coli*. These plasmids were transformed into the *E. coli* hosts using methods similar to those described in Example 2 for *B. subtilis*. The *E. coli* cells harboring the plasmids are resistant to ampicillin as a result of the production of the *B. licheniformis* beta-lactamase enzyme. This is demonstrated by means of the PVA plate assay developed by Sherratt and Collins, supra.

When the *B. licheniformis* beta-lactamase gene carrying plasmids are propagated in *E. coli*, the secreted form of the enzyme is not transported into the culture medium as it is in *B. subtilis*. Since *E. coli* has an outer membrane surrounding the limiting cytoplasmic membrane, the beta-lactamase exoenzyme was allowed to accumulate in the periplasmic space and was then harvested by appropriate methods.

EXAMPLE 4

The beta-lactamase gene of *B. licheniformis* is not the only source of a signal peptide sequence that can function in *B. subtilis* or *E. coli*. As indicated above, many proteins (especially in eucaryotic cells) are transported across membranes. Although the precise amino acid sequence of the "signal region" may, and in fact does, vary among different transported proteins, the folded structures of these regions, which can be predicted according to the rules of Chou and Fasman (*Ann. Rev. Biochem.* (1978) 47:251), are very similar. Thus, the requirements for a transport signal peptide sequence can be satisfied with non-*Bacillus* signal peptides, provided the signal sequence encoding DNA fragment is correctly positioned downstream from a Bacillus promoter, and ribosome binding site sequence.

One such eucaryotic transport signal sequence that may be used in connection with a desired gene product is the signal or presequence preceding the insulin B chain. (The various insulin chains A, B, and C, are made as single polypeptides and are assembled and processed in the endoplasmic reticulum on the way to being exported by the cell). However, in the insulin presequence there is no convenient restriction site immediately after the signal peptide sequence which can be used to join it with a cloned gene of heterologous DNA. Nevertheless, the last five nucleotides of the signal sequence in insulin are AGGCT and the first nucleotide of the insulin B chain itself is T. These six nucleotides together (AGGCTT) differ by a single nucleotide from AAGCTT which is the recognition sequence for the restriction enzyme HindIII The enzyme cuts between the two As. If the heterologous DNA was cloned or separated using the same enzyme, HindIII, or using a half HindIII site bifunctional linker, the sequence will be restored when the heterologous DNA is inserted.

The single nucleotide $G_X$ may be changed to an A to provide the HindIII site by the procedure described by Bahl in U.S. Pat. No. 4,351,901. In this procedure, the nucleotide to be changed is exposed, altered, and the sequence reconstructed. Alternatively, a small single stranded fragment incorporating the change is synthesized by the method of Narang et al. (*Canadian Journ. of Chem.* (1973) 51 3649) In either case, this change results in no alteration of the next to last amino acid of the signal sequence.

DNA ligation may be accomplished as described by Hershfield et al., supra. Reverse transcriptase may be used as a DNA polymerase such as described by Bahl et al. (*Proc. Natl. Acad. Sci., USA* (1977) 74:966). Transformation may proceed as described by Cohen et al. (*Proc. Natl. Acad. Sci., USA* (1973) 70:3240).

EXAMPLE 5

Although the procedure described in Example 4 above is technically feasible, it is a eukaryotic leader sequence and thus the procedure may be useful only in connection with general research. Typically, a more useful approach from a commercial standpoint is in connection with a prokaryotic (bacterial) host. Although only a few such signal sequences are known in connection with prokaryotic systems, one sequence which is will characterized is the sequence from TEM betalactamase. (Sutcliffe, *Proc. Natl. Acad. Sci., USA* (1978) 75:3737) This sequence is ideal for attaching to a cloned gene except that there is no convenient restriction site at the location for presequence processing. The nearest restriction site to the signal sequence is an MboI site which would result in the attachment of 16 extraneous amino acids to the cloned gene product.

Nevertheless, the terminal portion of the signal sequence, which is TTTGCT, may be altered, by one of the above-described techniques, to TTGAT. When the latter sequence is read along with the first few following nucleotides of the TEM beta-lactamase gene, a restriction site for BclI (TGATCA) exists. This results in the altering of the final amino acid from Ala to Asp and in the attaching of one extra amino acid to the gene product, either a Glu or His, depending upon what the first attached nucleotide of the heterologous DNA is.

To accomplish the foregoing alteration in nucleotides, the approach described above may be used wherein a short fragment is synthesized. There are bracketing restriction sites upstream from the signal sequence (ThaI) and a restriction site MboI, as mentioned above, downstream. A TaqI site exists even further downstream. Restriction conditions may be followed for ThaI as described by McConnell et al., *Nucleic Acid Res.* (1978) 5:1729; for MboI by Galinas et al., *J. Mol. Biol.* (1977) 114:169; or TaqI by Sato et al., *Proc. Natl. Acad. Sci., USA* (1977) 74:542. Note that in connection with MboI, the DNA is prepared in the host cell GM119 which lacks deoxyadenosine methylase (to avoid methylation of regions and prevent MboI cutting). In this latter connection see Marinus et al., *Mutat. Res.* (1975) 28:15. Alternatively, the restriction endonuclease Sau3A, an isoschizome of MboI, may be used with DNA isolated from any host.

EXAMPLE 6

The expression of pencillinase (penP) from *Bacillus licheniformis* is known to be under the control of a repressor. The repressor gene, penI, was subcloned from the 4.2 kb EcoRI fragment of plasmid pTB2 by digesting the EcoRI fragment with NdeI, repairing the staggered ends with Klenow polymerase I fragment in the presence of all four dNTPs, and then cutting with SstI restriction enzyme. The ~797 bp NdeI(blunt end)-SstI fragment was ligated with T4 DNA ligase to SmaI and SstI digested plasmid pUC18 (Yanisch-Perron et al., *Gene* (1985) 33:109–119) to construct plasmid pWW1. Dideoxy sequencing of pWW1 revealed three nucleotide changes from the sequence published by Himeno et al., supra. All three changes fell within the penI coding sequence These differences correspond to T→C, G→T, and G→C, at positions 509, 800, and 801, respectively numbered in accordance with FIG. 7. The penI$^c$ protein has proline, isoleucine, and leucine in place of serine, methionine, and valine, at the corresponding amino acid positions (34, 97, and 98, respectively). Primers for oligonucleotide-directed, site specific mutagenesis were designed to change the sequence of the 749/C repressor (penI$^c$), which constitutively expresses penP, to the wild-type (penI+) sequence (VW11 and VW12) and to insert a HindIII site (VW14), at the 5' end of the gene just preceding the ATG initiation codon, and a BamHI site (VW13), at the 3, end of the gene just after the TGA stop codon. The primers are listed below:

VW11: CTGGTTTTGGATAACTCTTTAATTACC
VW12: CCAAAAAGTTTAATACCATCGAATTAAGAG
VW13: GGAATAAAGAAAGAACTGGGATCCTCATTCCTT CTTTC
VW14: GAGGTATTTTTTTCATAAGCTTCATCCTATACTTAC

In addition, HindIII-BamHI penI cassettes were also constructed for the penI$^c$ gene sequence (using primers VW13 and VW14) as well as HindIII-BamHI penI cassettes for the penI Pro$_{34}$→Ser gene sequence (using primers VW11, VW13 and VW14) and the penI Ile$_{97}$→Met, Leu$_{98}$→Val gene sequence (using primers VW12, VW13 and VW14). All four HindIII-BamHI cassettes containing the various penI genes were individually subcloned into HindIII- and BamHI-digested plasmid pAW740 (ATCC 53165) so as to be under the control of the p$_L$ promoter and the N gene ribosome binding site. *E. coli* strain DG116 (ATCC 53606) which carries the lambda cI857 temperature sensitive repressor, was the host for hyperproduction of the repressor.

Upon heat induction, the *E. coli* transformants efficiently expressed the penI protein (predicted MW 14,983) and the protein was purified according to the method of Johnson et al., *Methods in Enzymol.* (1980) 65:842–845 with the following modifications. One thousand A$_{600}$ units of heat-induced cells were resuspended to approximately 7.3 ml in lysis buffer (100 mM Tris-HCl pH 8, 200 mM KCl, 1 mM EDTA, 2 mM CaCl$_2$, 10 mM MgCl$_2$, 0.1 mM dithiothreitol and 5 % glycerol) and sonicated in a cup sonicator. The sonicate was then diluted to 20 ml with standard buffer (SB contains 10 mM Tris-HCl, pH 8, 2 mM CaCl$_2$, 0.1 mM EDTA, 0.1 mM DTT and 5% glycerol) containing 200 mM KCl for polyethyleneimine precipitation. Ammonium sulfate precipitation was done in two steps, one at 35%(w/v) and the second at 50%(w/v). Precipitates from these steps were resuspended in SB and 50 mM KCl and dialyzed against the same without the additional salts. The resulting sample (including precipitates) were centrifuged and the supernatant discarded. The precipitates were washed twice with cold SB containing 50 mM KCl and resuspended in same. The precipitate from the 50% ammonium sulfate cut contained the majority of the repressor protein at approximately 95% purity as judged by Coomassie stained SDS-PAGE analysis.

Nuclease contamination in the purified penI+protein was examined by incubating 50 picomoles of purified repressor protein with one picomole of supercoiled or digested plasmid DNA overnight at 37° C. No nuclease activity was detected in either sample. This protein was used to demonstrate specificity of binding to a fragment containing the operators upstream of the penP gene on plasmid pSYC667 (Wong and Chang, *Proc. Natl. Acad. Sci. USA* (1986)83:3233-3237).

Plasmid pSYC667 is an *E. coli* and *B. subtilis* bifunctional vector which contains the gene for penP. The vector contains 3 ClaI fragments (4.8, 3.1, and 1 kb; the smallest fragment carries the two putative operators of the penP gene. Wild-type repressor protein was mixed with ClaI-digested pSYC667 DNA at molar ratios of protein to DNA ranging from 16:1 to 2:1 and incubated in SB containing 200 mM KCl for 30 min at 37° C. before fractionation on an agarose gel. The mobility of the 1 kb fragment was significantly affected at the highest protein:DNA ratio and the retardation was apparent even at the lower ratios while the mobility of the larger fragments did not change. Thus, the penI protein specifically binds to the operator when the protein is present at low concentration.

To demonstrate the exact nucleotides to which the repressor binds, DNAseI protection or footprinting experiments were undertaken. A 316 bp Sau3A fragment containing the three operators was subcloned from the 4.2 EcoRI fragment and subcloned into BamHI digested pUC13 (P. L. Biochemicals, Milwaukee, WI) to construct a vector designated pVW7. The operator fragment can be excised from this plasmid by cutting with HindIII and EcoRI. Digestion with HindIII (followed by treatment with alkaline phosphatase) and EcoRI of pVW7 generates a 365 bp fragment which was used in the footprinting experiments. Experiments at protein:DNA ratios of approximately 200, 100 or 50:1 demonstrated complete protection of two sections of the labelled fragment. As shown in FIG. 7 there is a 51 bp protected sequence representing the two operators preceding the penP gene and a 33 bp protected sequence representing the operator preceding the penI gene.

EXAMPLE 7

In order to test whether the penI gene could regulate the expression of a heterologous protein, a series of plasmid vectors were constructed.

Plasmid pTW75 was used as the vector fragment for the insertion of the penI coding cassettes. This plasmid was constructed from two plasmids, pLP1201-RBS1 and pLP1201-p156-RBS1, described in U.S. Pat. 4,666,848, and incorporated herein by reference. Briefly, LP1201-RBS is an *E. coli* and *B. subtilis* derived bifunctional vector which contains a synthetic ribosome binding site. Promoter 156, which is recognized by *B. subtilis* vegetation RNA polymerase and cloned from bacteriophage SP82, was subcloned as an EcoRI restriction fragment into the EcoRI site of pLP1201-RBS1 to form pLP1201-p156-RBS1.

To eliminate two additional BamHI restriction sites which border the p156 promoter, plasmid pLP1201p156-RBS1 was digested to completion with BamHI and treated with S1 nuclease to generate blunt ends and the 156 base pair fragment was isolated by acrylamide gel electrophoresis. This fragment was subcloned into SmaI-digested pLP1201-RBS1 to form pTW75. *E. coli* strain MM294 was transformed with plasmid pTW75 using conventional methods and *E. coli* transformants carrying the plasmid pTW75 were ampicillin and tetracycline resistant.

The four previously constructed HindIII-BamHI DNA cassettes containing the penI coding regions were cloned into HindIII and BamHI digested plasmid pTW75, resulting in the construction of pVW25 (penI$^c$); pVW26 (penI Pro$_{34}$→Ser); pVW27 (penI Ile$_{97}$→Met and Leu$_{98}$→Val); and pVW28 (pen+).

The four plasmids pVW25-28 were individually digested to completion with EcoRI and the ends were repaired with Klenow polymerase I in the presence of all four dNTPs, followed by digestion with BamHI restriction enzyme. The small fragments carrying the p156-RBS1-penI sequences were separately subcloned into the HindIII (blunt-end repair) and BamHI sites of plasmid pACYC184 (ATCC 37033) to generate the following four vectors: pHCW-P1 (penI$^c$); pHCW-P2 (penI Pro$_{34}$→Ser); pHCW-P3 (penI Ile$_{97}$→Met, Leu$_{98}$→Val); and pHCW-P4 (penI+). Plasmid pACYC184 is an *E. coli* plasmid conferring resistances to chloramphenicol and tetracycline. The replicon is compatible with pBR322.

Next, the vectors were individually tested for the ability of the respective penI proteins to regulate the transcription of a heterologous protein mRNA initiated from the penicillinase operator and promoter. For the transformation experiment, these vectors were complemented with a vector containing a compatible *E. coli* replicon, the penicillinase operator and promoter and a heterologous gene. For example, plasmid pJM15 contains the pBR322 replicon and the pen operator and promoter region ligated to a beta-interferon-lacZ fusion gene and was used in this experiment. However, one can easily substitute a variety of known vectors for pJM15, such as pMC306 (Casadaban and Cohen, *Gen. Microbiol.* (1980) 138:179-207). The penP promoter can be subcloned on an EcoRI-PstI fragment which has been made blunt-ended into the unique SmaI site of plasmid pMC306. The resulting plasmid would contain all the necessary components found on pJM15, such as the penP operator and promoter, the lacZ gene and ribosome binding site and the pBR322 replicon. Either of these two vectors can be used with the pHCW-P1 to P4 vector series to transform *E. coli* MC1000 (ATCC 39531), a Lac$^-$host, and assayed for expression of beta-galactosidase.

In this experiment, *E. coli* pVW25 transformants produced dark blue colonies on X-gal indicator plates, while *E. coli* bacteria transformed with pVW26 or pVW27 produced light blue colonies, and pVW28 transformants produced white colonies, indicating that the penI repressor protein encoded by the respective genes on these plasmids (penI Pro$_{34}$→Ser; penI Ile$_{97}$→Met, Leu$_{98}$→Val; and penI+) were functional and could bind to the operator to regulate transcription initiation of the betagalactosidase fusion gene.

It may be seen, therefore, that the invention provides a method and a vector for the controlled accumulation of heterologous cloned gene products. The products are transferred or transported outside the host cell, enabling the harvesting of the product to proceed with minimal restrictions, and avoiding the likelihood of degradation or destruction of either the host cell or the gene product itself.

Various modifications of the invention in addition to those shown and described herein will become apparent to those skilled in the art from the foregoing description and accompanying drawings. Such modifications are intended to fall within the scope of the appended claims.

We claim:

1. A bacterial vector capable of regulating expression of a predetermine heterologous protein, said vector comprising a gene encoding said predetermined protein, said gene operably linked to a promoter, wherein said promoter is regulated by an operator that binds a functional repressor protein encoded by a penI gene and wherein said operator comprises a pair of inverted repeat sequences and is selected from the group consisting of operators encoded by the penP and penI genes of *Bacillus licheniformis*.

2. The bacterial vector according to claim 1 wherein said functional penI protein encoded by the penI gene is selected from the group consisting of penI$^+$; penI Pro$_{34}\rightarrow$Ser; and penI Ile$_{97}\rightarrow$Met, Leu$_{98}\rightarrow$Val.

3. The bacterial vector of claim 1 wherein the promoter is the penP promoter of *Bacilius licheniformis*.

4. The bacterial vector of claim 1 wherein said repressor is encoded by a gene located on a plasmid.

5. The bacterial vector of claim 1 wherein said repressor is encoded by a gene integrated in the chromosome of a microorganism transformed with the vector.

6. A microorganism transformed with the bacterial vector of claim 1.

7. The microorganism of claim 6 which is *E. coli*.

8. The microorganism of claim 6 which is *B. subtilis*.